United States Patent [19]

Guillemet et al.

[11] Patent Number: 4,837,025

[45] Date of Patent: Jun. 6, 1989

[54] SELF-ADHESIVE DEVICE FOR THE PERCUTANEOUS ADMINISTRATION OF AN ACTIVE INGREDIENT

[75] Inventors: Alain Guillemet, Dijon; Eric Teillaud, Talant; Philippe Reginault, Fontaine les Dijon; Bruno Bevan, Dijon, all of France

[73] Assignee: Laboratoires D'Hygiene et de Dietetique, Paris, France

[21] Appl. No.: 247,852

[22] Filed: Sep. 22, 1988

Related U.S. Application Data

[63] Continuation-in-part of Ser. No. 174,414, Mar. 25, 1988.

[51] Int. Cl.$^4$ .............................................. A61K 9/16
[52] U.S. Cl. .................... 424/448; 424/449; 424/486
[58] Field of Search ............ 424/448, 449, 486

[56] References Cited

U.S. PATENT DOCUMENTS

| | | | |
|---|---|---|---|
| 4,615,699 | 10/1986 | Gale et al. | 424/448 |
| 4,738,848 | 4/1988 | Yoshida et al. | 424/448 |
| 4,740,374 | 4/1988 | Nakano et al. | 424/448 |
| 4,746,509 | 5/1988 | Haggiage et al. | 424/449 |
| 4,764,515 | 8/1988 | Borsa et al. | 514/255 |
| 4,776,850 | 10/1988 | Guse et al. | 424/486 |
| 4,784,856 | 11/1988 | Fukuda et al. | 424/448 |

FOREIGN PATENT DOCUMENTS 0159168 10/1985 European Pat. Off. .

OTHER PUBLICATIONS

Patent Abstracts of Japan, vol. 10, No. 144 (C-349)[2201], May 27, 1986.
JP-A-61 5012, Daiichi Seiyaku K.K., Jan. 1, 1986.

*Primary Examiner*—Thurman K. Page
*Attorney, Agent, or Firm*—Holman & Stern

[57] ABSTRACT

The present invention relates to a novel self-adhesive matrix for the percutaneous administration of a pharmaceutical active ingredient. This matrix comprises a combination of the following:

(a) 30 to 50 parts by weight of an ethylene/vinyl acetate copolymer material,
(b) 20 to 45 parts by weight of a higher aliphatic monoalcohol compound,
(c) 5 to 20 parts by weight of a cellulose derivative material,
(d) 1 to 20 parts by weight of an ester compound of a polyhydric alcohol with a fatty aliphatic acid, and
(e) 0.1 to 20 parts by weight of an active ingredient which can be administered percutaneously.

14 Claims, No Drawings

SELF-ADHESIVE DEVICE FOR THE PERCUTANEOUS ADMINISTRATION OF AN ACTIVE INGREDIENT

CROSS REFERENCE

This invention is a continuation-in-part of U.S. Pat. application Ser. No. 07/174,414 filed on March 25, 1988.

FIELD OF THE INVENTION

The present invention relates to a novel matrix for the percutaneous administration of a pharmaceutical active ingredient.

The term matrix is understood here as meaning the chemical composition of ingredients enabling the percutaneous administration of an active ingredient, and the term device is understood as meaning the whole consisting of the matrix and its support.

The parent application was concerned with a matrix comprising a') 40 to 60 parts by weight of an ethylene/vinyl acetate copolymer material, b') 40 to 60 parts by weight of a higher aliphatic monoalcohol compound, c') 1 to 20 parts by weight of a cellulose derivative material, d') 0.1 to 8 parts by weight of a polyhydric alcohol compound, and e') 0.01 to 10 parts by weight of an active ingredient which can be administered percutaneously, the weight ration (a'+c') / (b'+d') being betweeing 0.7 and 1.3.

This invention is concerned with a new matrix w herein, in particular, means d'), i.e. the polyhydric aocohol compound, is replaced by an ester compound obtained by reaction of a polyhydric alcohol with a fatty aliphatic acid.

PRIOR ART

Numerous systems have already been proposed for the percutaneous administration of an active ingredient. In particular, systems for the percutaneous administration of trinitroglycerol are known for the treatment of angina pectoris. These systems, which consist of a support on which a reservoir or matrix containing the active ingredient is deposited, have the disadvantage that their adhesiveness to the skin decreases rapidly with time. In fact, in the case of a reservoir, the active ingredient is dissolved in a solvent which serves to carry the active ingredient through a microporous membrane to the skin. In the case of a matrix, the active ingredient contained in a polymer lattice is also dissolved in a solvent which serves as a carrier. As the reservoir or matrix is held on the skin by a conventional adhesive of the acrylic type, the solvent partially dissolves some of the components of the adhesive, which thus rapidly loses its effectiveness.

To overcome this disadvantage, European Patent Document A-O No. 159168 has already proposed a solution whereby the matrix containing the active ingredient has properties of self-adhesion to the skin. This matrix, containing an active ingredient, consists of a water-soluble protein, a polyhydric alcohol compound, a tackifier and an oleaginous substance. More particularly, the water-soluble protein can be natural of synthetic and animal or vegetable, for example gelatin, collagen, casein or bird lime, in proportions of 5 to 50%; the polyhydric alcohol compound can be a glycol compound, for example ethylene glycol, propylene glycol, butylene glycol or polyethyleneglycol, a triol compound or a polyol compound, in proportions of 5 to 50%; the tackifier can be cellulose or a derivative material, for example methyl cellulose, ethyl cellulose, propyl cellulose, methylpropyl cellulose, hydroxymethyl cellulose, hydroxypropyl cellulose or carboxymethyl cellulose, a polysaccharide compound, polyvinyl alcohol or polyvinylpyrrolidone, in proportions of 0.1 to 15%; and the oleaginous substance can be a fatty acid ester, paraffin, lanolin, a higher aliphatic monoalcohol compound, for example, octyldecyl, palmityl, stearyl or myristyl alcohol, or silicone oil, in proportions of 0.1 to 25%.

An example of a matrix which contains glycerol monolaurate as a permeation promoting agent is disclosed in U.S. Pat. No. 4,746,515. In that patent document the glycerol monolaurate material represents 25% by weight of a matrix which comprises 36% by weight of an EVA 40 product (i.e. a product having 40% by weight of vinyl acetate units).

OBJECT OF THE INVENTION

Now a novel technical solution is provide; it involves the use of a self-adhesive matrix which differs from the prior art teaching of EP-A-O No. 159168 by the nature of the main constituent, by the proportions of the other constituents and also by the ease of industrial processing. This novel technical solution also differs from the prior art teaching of U.S. Pat. No. 4,764,515 by the fact that the constituents of liquid phase of the matrix according to this invention are used in such an amount that they are not used as permeation promoting agents, but as solvents of the active ingredient to be administered per percutaneous route.

The self-adhesive matrix according to the invention for the percutaneous administration of an active ingredient comprises a) 30 to 50 parts by weight of an ethylene/vinyl acetate copolymer material, b) 20 to 45 parts by weight of a higher aliphatic monoalcohol compound, c) 5 to 20 parts by weight of a cellulose derivative material, d) 1 to 20 parts by weight of an ester compound of a polyhydric alcohol with a fatty aliphatic acid, and e) 0.1 to 20 parts by weight of an active ingredient which can be administered percutaneously.

DETAILED DISCLOSURE OF THE INVENTION

Advantageously, the ethylene/vinyl acetate (EVA) copolymer material used will have a content of vinyl acetate units of between 35 and 55% by weight, preferably of the order of 45% by weight, relative to the weight of the ethylene/vinyl acetate copolymer material.

The term higher aliphatic monoalcohol compound is understood here as meaning saturated or unsaturated monoalcohol compounds having 12 to 20 carbon atoms, for example 2-cotyldodecan-1-ol, palmityl alcohol, stearyl alcohol or myristyl alcohol.

The term cellulose derivative material is understood here as meaning alkyl celluloses, for example methyl cellulose, ethyl cellulose, propyl cellulose or methylpropyl cellulose, and hydroxyalkyl celluloses, for example hydroxymethyl cellulose, hydroxyethyl cellulose or hydroxypropyl cellulose.

The term ester compound of a polyhydric alcohol with a fatty aliphatic acid is understood here as meaning an ester compound obtained from (i) a polyhydric alcohol component, in particular glycerol and any glycol compound, and more particularly alkylene glycols, such as for instance ethylene glycol, propylene glycol, dipropylene glycol, butylene glycol, triethylene glycol, diethylene glycol, polyethyleneglycol and polypropyleneglycol, and (ii) and aliphatic fatty acid component having from 8 to 18 carbon atoms, such as for instance pelargonic acid, stearic acid, isostearic acid, capric acid, caprylic acid, palmitic acid, lauric acid, myristic acid and oleic acid.

The term active ingredient is understood here as meaning any solid or liquid product which can be administered percutaneously and which is at least partially soluble in the phase comprising or consisting of means b) and d). Preference will be given to non-steroid anti-inflammatory products such as ibuprofen, ketoprofen, niflumic acid or mefenamic acid, calcic antagonists of the dihydropyridine type, such as nifedipine or nicardipine, β-blocking agents, such as timolol or propranolol, and β-stimulating agents, such as for instance procaterol or salbutamol.

In practice, preference will be given to an active ingredient amount which is such that said active ingredient saturates the liquid phase consisting of means b) and d), and preference will be given to formulations which are such that the weight ratio of the solvent phase [means b) and d)] to the polymer phase [means a) and c)] is about one.

The support receiving the matrix may be any flexible support which is impermeable to the constituents of the matrix and which has a thickness of between 50 and 100 micrometers. Preference will be given to a polymeric support, such as for example (i) polyethylene, polypropylene, polyesters, (ii) foams, especially microcellular ones, such as polyethylene foams which are known in particular in the field of bandages and wound dressings, and (iii) copolymers obtained from at least 2 monomers selected from the group comprising ethylene, propylene, $C_1$–$C_3$ alkyl acrylates and $C_1$–$C_3$ alkyl methacrylates.

In practice, the matrix may be covered with a protective film which can be peeled off before the device is used, and the device itself may be packaged in a leak-tight form of protection, for example a polyethylene/aluminium composite.

The self-adhesive device according to the invention for the percutaneous administration of an active ingredient either does not stick or does exhibit a very low sticking power (i.e. "tackyness") immediately on contact with the skin but has a progressive adhesive strength which increases a few minutes after it has been placed on a subject's skin. The device or matrix can easily be removed without desquamation of the skin and then put back, retaining an identical adhesive strength. This is particularly advantageous for a device of this type which is subject has to keep on for several days; he can thus remove the said device temporaly, for example when taking a bath.

The device according to the invention has the further advantage of being reduced to a minimum area and a minimum thickness. By virtue of its own adhesive strength, it is not necessary to apply an adhesive compound around the edge of the active part of the device. The whole surface of the device is both active and adhesive. Thickness of a few hundred micrometers of matrix (150 to 250 micrometers with a corresponding weight of from 100 to 300 g/cm$^2$) will suffice to administer the necessary amount of active ingredient through the skin for several days.

According to the invention, a method for the preparation of a self-adhesive matrix for percutaneous administration of an active ingredient is recommended which comprises the following steps:

1) the means a) and part of the means b) are mixed, with stirring, at a temperature greater than or equal to 110° C., and the resulting mixture is homogenized for about 0.5 h, 2) the means c) is incorporated per small portions into the homogenized mixture resulting from stage 1, with stirring, at a temperature greater than or equal to 110° C., then the resulting mixture is homogenized, 3) the remainder of the means b) is incorporated into the homogenized mixture resulting from stage 2, with stirring, at a temperature greater than or equal to 110° C., 4) the resulting mixture thus obtained is homogenized at a temperature greater than or equal to 110° C. and then left to stand for at least 8 hours, 5) the homogenized resulting mixture thus obtained is heated at a temperature of 50°–70° C. (preferably 60° C.) for at least 0.25 h, after which the means d) and the active ingredient in a solvent for the said active ingredient, for example ethanol, are incorporated at said temperature of 50°–70° C. (preferably 60° C.), said solvent representing from 30 to 100% v/w (preferably 80% v/w) with respect to the total weight of means a), b), c), d) and e), 6) the resulting mixture is homogenized for at least 0.5 h at a temperature of 50°–70° C. (preferably 60° C.), 7) the homogenized resulting mixture thus obtained is deposited on a temporary support, especially silicone-treated paper, at a temperature of the order of 50°–70° C., at a rate of 100 to 300 g/m$^2$, for obtaining an assembly consisting of said temporary support and the matrix deposited thereon, 8) the whole assembly consisting of said temporary support and said matrix is heated at a temperature of the order of 70°–90° C. in order to evaporate the solvent for the active ingredient until the residual proportion is less than 5%, and 9) the resulting dry matrix is transferred onto an appropriate support.

The industrial production of the device according to the invention is facilitated by the fact that the matrix charged with active ingredient is malleable and cal also be coated onto a support by the so-called "fusion" technique, i.e. by fusion in the absence of solvent. Whichever coating technique is employed (solvent phase of "fusion" technique), it is thus possible to coat large areas and then cut the device to the desired size, which is calculated according to the amount of active ingredient present per unit area and the amount of active ingredient to be administered to the subject over a given time.

This simple manufacturing technique of cutting to a variable area is particularly advantageous for marketing device for different sizes, capable of administering different amounts of active ingredient. It is known in fact that, for certain active ingredients, especially β-blocking agents and β-stimulating agents, the daily posology must be adapted to each subject in function of the clinical results which are obtained. In particular with the device according to the invention, the dosage will be progressively increased or respectively reduced by using devices of increasing or respectively decreasing areas, for obtaining the therapeutical effect which is exactly expected.

Numerous devices according to the invention had been prepared and tested to study ex vivo the permeation kinetics on a disk of 3,14 cm² of nude ("hairless") mice abdominal skin in a glass static cell having a receiving compartment of a volume of 31 ml, stirred by means of a magnetic system and plunged in a thermostatic controlled bath at 37° C. In the following preparative examples are given average results obtained from 3 identical samples of each preparation.

PREPARARTION I

Example 1

1375 g of LEVAPREN 450P$^R$ (an EVA product having a content of vinyl acetate units of 45%, commercialized by BAYER) and 840 g of EUTANOL G$^R$ (2-octyldodecanol commercialized by HENKEL) are introduced into a 5-liter malaxator. The temperature is raised to 140° C. in 0.5 h and 305 g of ETHOCEL 20$^R$ (ethyl cellulose with a viscosity of $2 \times 10^{-2}$ Pa.s, commercialized by DOW CHEMICAL) are added in small portions to the resulting mixture. After homogenization of the medium, 420g of EUTANOL G$^R$ are added. The whole is homogenized for 0.5 hour and left to stand for 24 hours. The composition thus obtained is then heated at 60° C. for 0.5 hour and a solution of 350 g of LAUROGLYCOL$^R$ (a mixture of propylene glycol lauric acid mono- and diester commercialized by the firm GATTEFOSSE) and 210 g of niflumic acid in 1910 g of anhydrous ethanol. The resulting mixture is homogenized for 1 h at 60° C. The mass thus obtained is coated onto a 105 mm wide piece of silicone-treated paper at a temperature of 60° C. at at a rate of 148±5 g/m². After the coated silicone-treated paper has been heated to 80° C. in order to evaporate the ethanol to a content lower than 3.5%, the matrix is transferred onto a polyethylene support.

RESULTS

Matrix composition means a) : 39.3%
means b) : 36%
means c) : 8.7%
means d) : 10%
means e) : 6%
does of active ingredient : 888 μg/cm²

Average data obtained by ex vivo permeation kinetics eluant : physiological serum [NaCl at 0.9% /PEG 400 (80/20) v/v]
amount of active ingredient absorbed in a 24 h period of time : 29.2%
means flow : 11.6 μg/cm²/h±12.3%

PREPARATION II

Example 2

According to the method disclosed in Preparation I, with the exception that the LAUROGLYCOL$^R$ product was replaced by the same quantity of LABRASOL$^R$ [a mixture of (i) esters of caprylic and capric acids with glycerol and (ii) PEG 400, commercialized by the firm GATTEFOSSE] and that coating was carried out at a rate of 138±5 g/m², a matrix coated onto a polyethylene support was obtained.

RESULTS

Matrix composition means a) : 39.3%
means b) : 36%
means c) : 8.7%
means d) : 10%
means e) : 6%
does of active ingredient : 828 μg/cm²

Average data obtained by ex vivo permeation kinetics eluant : physiological serum [NaCl at 0.9% /PEG 400 (80/20 v/v]
amount of active ingredient absorbed in a 24 h period of time : 32.6%
means flow : 12.1 μg/cm²/h±6.8%

PREPARATION III

Example 3

1505 g of LEVAPREN 450P$^R$, 925 g of EUTANOL G$^R$ and 330 g of ETHOCEL 20$^R$ are mixed at 140° C., analogously to Preparation I, and 460 g of EUTANOL G$^R$ are then added. Then are added at 60° C. 105 g of MIGLYCOL 840$^R$ (a mixture of diesters of capric and caprylic acids with propylene glycol, commercialized by DYNAMIT NOBEL) and 175 g of ibuprofen of 1910 g of anhydrous ethanol. The subsequent procedure is identical to that of preparation I, with a coated mass of 181 ±5 g/m².

RESULTS

Matrix composition means a) : 43%
means b) : 39.5%
means c) : 9.5%
means d) : 3%
means e) : 5%
dose of active ingredient : 905 μg/cm²

Average data obtained by exvivo permeation kinetics eluant : phosphate buffer (pH 7.4)
amount of active ingredient absorbed in a 24 h period of time : 56%
means flow : 22.8 μg/cm²/h±19%

PREPARATION IV

Example 4

According to the method disclosed in Preparation III, with the exception that the MIGLYCOL 840$^R$ product was replaced by the same quantity of D.P.P.G$^R$ (propylene glycol dipelargonate, an ester compound commericialized by the firm GATTEFOSSE) and the coating was carried out at a rate of 183±5 g/m², a matrix coated onto a polyethylene support was prepared.

RESULTS

Matrix composition means a) : 43%
means b) : 39.5%
means c) : 9.5%
means d) : 3%
means e) : 5%
dose of active ingredient : 915 μg/cm²

Average data obtained by ex vivo permeation kinetics eluant : phosphate buffer (pH 7.4)
amount of active ingredient absorbed in a 24 h period of time : 62%
means flow : 25.4 µg/cm$^2$/h±19%

PREPARATION V

Example 5

1425 g of LEVAPREN 450P$^R$, 870 g of EUTANOL G$^R$ and 315 g of ETHOCEL 20$^R$ are mixed at 140° C. analogously to preparation I, then 435 g of EUTANOL G$^R$ are added. Then are added at 60° C. 105 g of D.P.P.G.$^R$ and 350 g of ibuprofen in 1910 g of anhydrous ethanol. The subsequent procedure is identical to that of Preparation I with a coated mass of 164±5 g/m$^2$.

RESULTS

Matrix composition means a) : 40.7%
means b) : 37.3%
means c) : 9%
means d) : 3%
means e) : 10%
dose of active ingredient : 1640 µg/cm$^2$ Average data obtained by ex vivo permeation kinetics eluant : phosphate buffer (pH 7.4)
amount of active ingredient absorbed in a 24 h period of time : 50%
means flow : 35.7 µg/cm$^2$/h±5%

PREPARATION VI

Example 6

1505 g of LEVAPREN 450P$^R$, 925 g of EUTANOL G$^R$ and 330 g of ETHOCEL 20$^R$ are mixed at 140° C., analogously to Preparation I, and 460 g of EUTANOL G$^R$ are then added. Then are added at 60° C. 105 g of LAUROGLYCOL$^R$ and 175 g of nifedipine in 1910 g of anhydrous ethanol. The subsequent procedure is identical to that of preparation I, with a coated mass of 125±5 g/m$^2$.

RESULTS

Matrix composition means a) : 43%
means b) : 39.5%
means c) : 9.5%
means d) : 2.9%
means e) : 5%
dose of active ingredient : 625 µg/cm$^2$ Average data obtained by ex vivo permeation kinetics eluant : physiological serum [NaCl at 0.9% /PEG 400 (70/30) v/v]
amount of active ingredient absorbed in a 24 h period of time : 6.4%
mean flow : 1.99 µg/cm$^2$/h±50%

PREPARATION VII

Example 7

1390 g of LEVAPREN 450P$^R$, 850 g of EUTANOL G$^R$ and 310 g of ETHOCEL 20$^R$ are mixed at 140° C. analogously to Preparation I, then 425 g of EUTANOL G$^r$ are added. Then are added at 60° C. 350 g of HYDROPHILOL ISOSTEARIQUE$^R$ (propylene glycol isostearate commercialized by the firm GATTEFOSSE) and 175 g of salbutamol in 1910 g of anhydrous ethanol. The subsequent procedure is identical to that of preparation I, with a coated mass of 102±5 g/m$^2$.

RESULTS

Matrix composition means a) : 39.7%
means b) : 36.5%
means c) : 8.8%
means d) : 10%
means e) : 5%
dose of active ingredient : 510 µg/cm$^2$ Average data obtained by ex vivo permeation kinetics eluant : physiological serm [NaCl at 0.9% /PEG 400 (70/30) v/v]
amount of active ingredient absorbed in a 24 h period of time : 83.5%
means flow : 18.44 µg/cm$^2$/h±10.6%

PREPARATION VIII

Example 8

According to the method of Preparation VII, with the exception that the HYDROPHILOL ISOTEARIQUE$^R$ product was replaced by the same quantity of LAUROGLYCOL$^R$ and that coating was carried out at a rate of 106±5 g/m$^2$, a matrix coated onto a polyethylene support was obtained.

RESULTS

Matrix composition means a) : 39.7%
means b) : 36.5%
means c) : 8.8%
means d) : 10%
means e) : 5%
dose of active ingredient : 530 µg/cm$^2$ Average data obtained by ex vivo permeation kinetics eluant : physiological serum [NaCl at 0.9% /PEG 400 (70/30) v/v]
amount of active ingredient absorbed in a 24 h period of time : 93.9%
mean flow : 20.35 µg/cm$^2$/h±4.9%

PREPARATION IX

Example 9

1309 g of LEVAPREN 450P$^R$, 800 of EUTANOL G$^R$ and 290 g of ETHOCEL 20$^R$ are mixed at 140° C., then 400 g of EUTANOL G$^R$ are added analogously to Preparation I. Then are added at 60° C. 350 g of MIGLYOL 840$^R$ and 350 g of timolol base in 1910 g of anhydrous ethanol. The subsequent procedure is identical to that of preparation I, with a coated mass of 283±5 g/m$^2$.

RESULTS

Matrix composition means a) : 37.4%
means b) : 34.3%
means c) : 8.3%
means d) : 10%
means e) : 10% dose of active ingredient : 2830 μg/cm²

Average data obtained by ex vivo permeation kinetics eluant : phosphate buffer (pH 7.4)
amount of active ingredient absorbed in a 24 h period of time : 73.6%
mean flow : 77.2 μg/cm²/h±11%

PREPARATION X

Example 10

According to the method of Preparation IX, with the exception that the MIGLYOL 840$^R$ product was replaced by the same quantity of HYDROPHILOL ISOSTEARIQUE$^R$ and that the coating was carried out at a rate of 273±5 g/m², a matrix coated onto a polyethylene support was obtained.

RESULTS

Matrix composition means a) : 37.4%
means b) : 34.3%
means c) : 8.3%
means d) : 10%
means e) : 10%
dose of active ingredient : 2725 μg/cm²

Average data obtained by ex vivo permeation kinetics eluant : phosphate buffer (pH 7.4)
amount of active ingredient absorbed in a 24 h period of time : 74%
mean flow : 74.9 μg/cm²/h±3.0%.

PREPARATION XI

Example 11

According to the method of Preparation IX, with the exception that the MIGLYOL 840$^R$ product was replaced by the same quantity of D.P.P.G.$^R$ and that the coating was carried out at a rate of 278±5 g/m², a matrix coated onto a polyethylene support was obtained.

RESULTS

Matrix composition means a) : 37.4%
means b) : 34.3%
means c) : 8.3%
means d) : 10%
means e) : 10%
dose of active ingredient : 2780 μg/cm²

Average data obtained by ex vivo permeation kinetics eluant : phosphate buffer (pH 7.4)
amount of active ingredient absorbed in a 24 h period of time : 73.3%
mean flow : 73.5 μg/cm²/h±1% .

What is claimed is

1. A self-adhesive matrix for the percutaneous administering of a pharmaceutical active ingredient comprising
    a) 30 to 50 parts by weight of an ethylene/vinyl acetate copolymer material,
    b) 20 to 45 parts by weight of a higher aliphatic monoalcohol compound,
    c) 5 to 20 parts by weight of a cellulose derivative material,
    d) 1 to 20 parts by weight of an ester compound of a polyhydric alcohol with a fatty aliphatic acid, and
    e) 0.1 to 20 parts by weight of an active ingredient which can be administered percutaneously.

2. A matrix according to claim 1 wherein the ethylene/vinyl acetate copolymer material has a content of vinyl acetate units of between 35 to 55% by weight, relative to the weight of said copolymer material.

3. A matrix according to claim 1 wherein the ethylene/vinyl acetate copolymer material has a content of vinyl acetate units of about 45% by weight, relative to the weight of said copolymer material.

4. A matrix according to claim 1 wherein the higher aliphatic monoalcohol compound is selected from the group consisting of saturated and unsaturated monoalcohol having from 12 to 20 carbon atoms.

5. A matrix according to claim 1 wherein the cellulose derivative material is selected from the group consisting of alkyl celluloses and hydroxyalkyl celluloses, in particular methyl cellulose, ethyl cellulose, propyl cellulose, methylpropyl cellulose, hydroxymethyl cellulose, hydroxyethyl cellulose and hydroxypropyl cellulose.

6. A matrix according to claim 1 wherein the ester compound of a polyhydric alcohol with a fatty aliphatic acid is selected from the group consisting of esters obtained from (i) a glycerol or glycol component and (ii) a fatty aliphatic acid component having from 8 to 18 carbon atoms.

7. A matrix according to claim 6 wherein the glycol component is selected from the group consisting of ethylene glycol propylene glycol, dipropylene glycol, butylene glycol, triethylene glycol, diethylene glycol, polyethyleneglycol and polypropyleneglycol.

8. A matrix according to claim 6 wherein the fatty aliphatic acid component is selected from the group consisting of pelargonic acid, stearic acid, isostearic acid, capric acid, caprylic acid, palmitic acid, lauric acid, myristic acid and oleic acid.

9. A matrix according to claim 1 wherein the active ingredient to be administered percutaneously is an anti-inflammatory agent, in particular ibuprofen, ketoprofen, niflumic acid or mefanamic acid.

10. A matrix according to claim 1 wherein the active ingredient to be administered percutaneously is a calcic antagonist of the dihydropyridine type, such as nifedipine or nicardipine.

11. A matrix according to claim 1 wherein the active ingredient to be administered percutaneously is a β-blocking agent, such as timolol or propranolol.

12. A matrix according to claim 1 wherein the active ingredient to be administered percutaneously is a β-stimulating agent, such as procaterol or salbutamol.

13. A matrix according to claim 1 wherein the weight ratio (a+c)/(b+d) is about 1.

14. A method for preparing a matrix as claimed in claim 1, coated on a support, said method comprising the following steps :
    1) the means a) and part of the means b) are mixed, with stirring, at a temperature greater than or equal to 110° C., and the resulting mixture is homogenized for about 0.5 h,
    2) the means c) is incorporated per small portions into the homogenized mixture resulting from stage 1, with stirring, at a temperature greater than or equal to 110° C., then the resulting mixture is homogenized,
    3) the remainder of the means b) is incorporated into the homogenized mixture resulting from stage 2, with stirring, at a temperature greater than or equal to 110° C.,
4) the resulting mixture thus obtained is homogenized at a temperature greater than or equal to 110° C. and then left to stand for at least 8 hours,
5) the homogenized resulting mixture thus obtained is heated at a temperature of 50°–70° C. for at least 0.25 h, after which the means d) and the active ingredient in a solvent for the said active ingredient, for example ethanol, are incorporated at said temperature of 50°–70° C., said solvent representing from 30 to 100% v/w with respect to the total weight of means a), b), c), d) and e),
6) the resulting mixture thus obtained is homogenized for at least 0.5 h at a temperature of 50°–70° C.,
7) the homogenized resulting mixture thus obtained is deposited on a temporary support, at a temperature of the order of 50°–70° C., at a rate of 100 to 300 g/m$^2$, for obtaining an assembly consisting of sad temporary support and the matrix deposited thereon,
8) the whole assembly consisting of said temporary support and said matrix is heated at a temperature of the order of 70°–90° C. in order to evaporate the solvent for the active ingredient until the residual proportion is less than 5%, and
9) the resulting dry matrix is transferred onto an appropriate support.

* * * * *